United States Patent [19]
Ingle et al.

[11] Patent Number: 4,664,124
[45] Date of Patent: May 12, 1987

[54] BIOLOGICAL FLUID SPECIFIC GRAVITY MONITOR WITH ULTRASONIC SENSOR CIRCUIT

[75] Inventors: Frank W. Ingle; Alan R. Selfridge, both of Palo Alto, Calif.

[73] Assignee: The Kendall Company, Boston, Mass.

[21] Appl. No.: 683,980

[22] Filed: Dec. 20, 1984

[51] Int. Cl.⁴ .............................................. A61B 6/00
[52] U.S. Cl. ................................... 128/660; 128/771
[58] Field of Search ......................... 128/660, 661, 771

[56] References Cited

U.S. PATENT DOCUMENTS

| | | | |
|---|---|---|---|
| 3,603,303 | 7/1971 | Stouffer | 128/660 |
| 3,967,490 | 7/1976 | Brady | 73/32 A |
| 4,020,330 | 4/1977 | Bae | 364/558 |
| 4,235,099 | 11/1980 | Ishizaka | 128/660 |
| 4,277,367 | 7/1981 | Madsen et al. | 128/660 |
| 4,343,316 | 8/1982 | Jespersen | 128/771 |
| 4,386,612 | 6/1983 | Röder et al. | 128/660 |
| 4,432,231 | 2/1984 | Napp et al. | 73/29 V |
| 4,448,207 | 5/1984 | Parrish | 128/771 |
| 4,522,068 | 6/1985 | Smith | 73/32 A |

FOREIGN PATENT DOCUMENTS 801836 2/1981 U.S.S.R. .............................. 128/660

OTHER PUBLICATIONS

Ultrasonics in Clinical Diagnosis by P. N. T. Wells Publisher: Churchill Livingstone, 1977.

*Primary Examiner*—Edward M. Coven
*Attorney, Agent, or Firm*—Donald N. Halgren

[57] ABSTRACT

An automatic urinary output monitor including a means for noninvasively determining the specific gravity of urine in a urine collection system including an oscillator with a feedback loop including ultrasonic transducers at opposite sides of a sampling chamber for producing an output signal with a frequency determined by the period of time it takes for a transmitted ultrasonic pulse to travel through the urine sample and to be received and means responsive to the frequency of the output signal for providing an indication of specific gravity of the urine sample.

6 Claims, 16 Drawing Figures

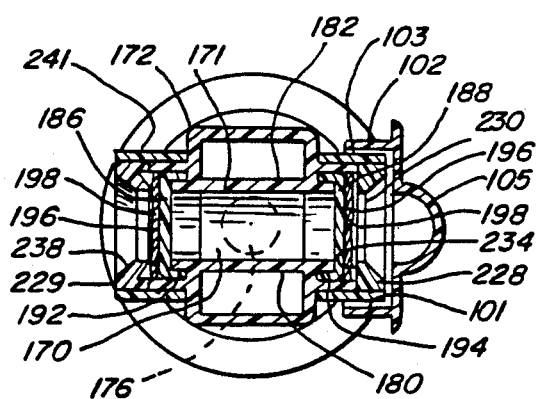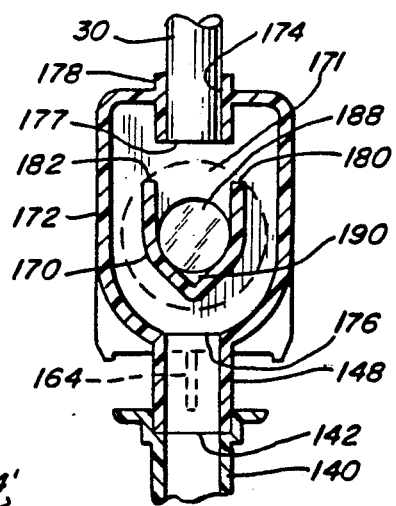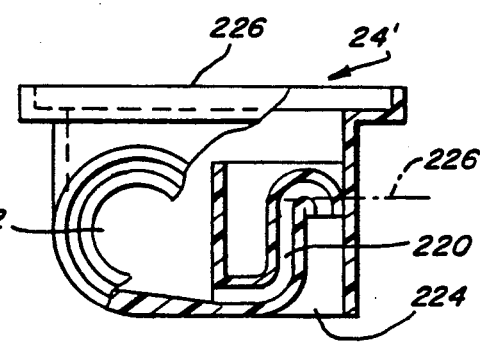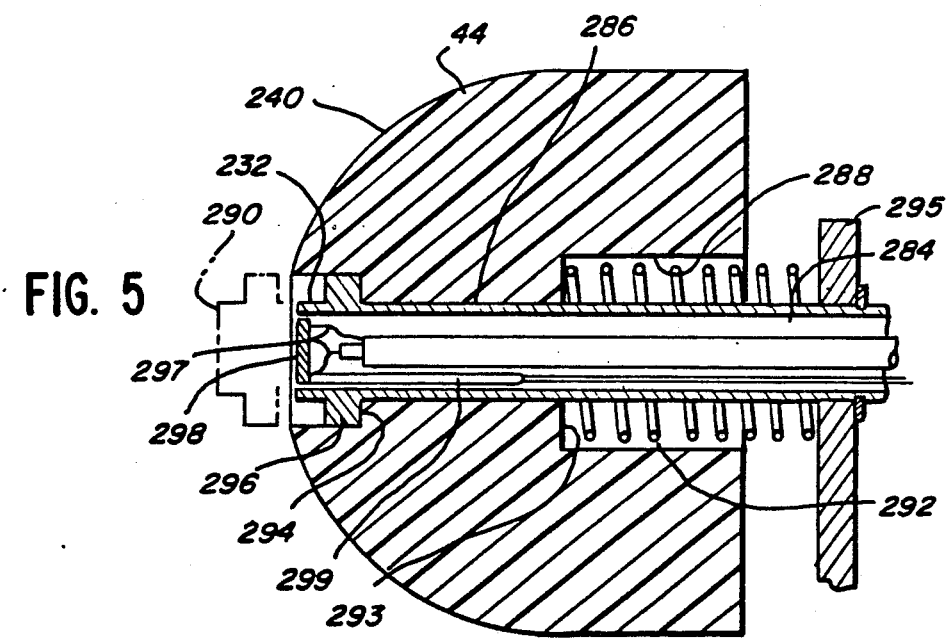

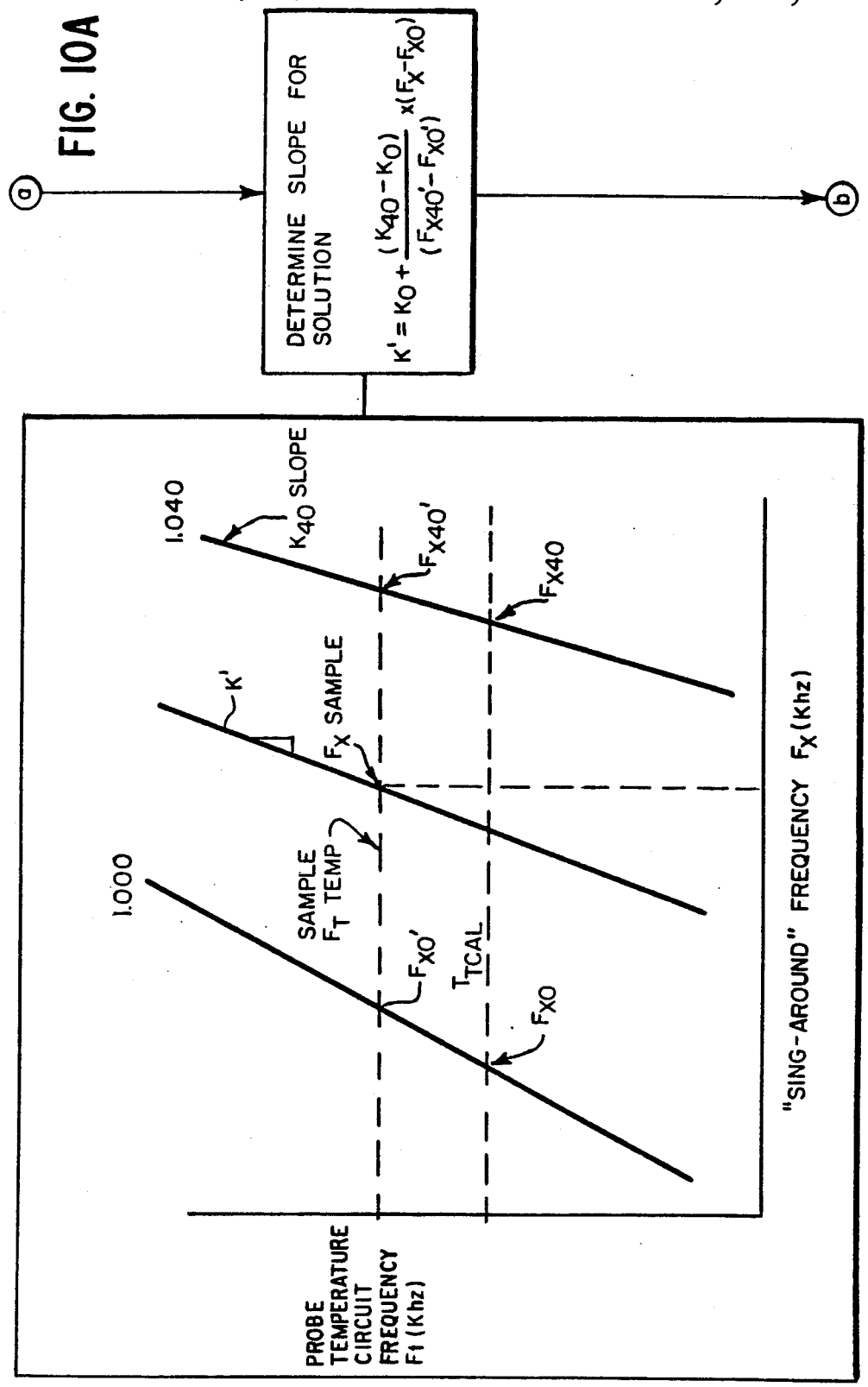

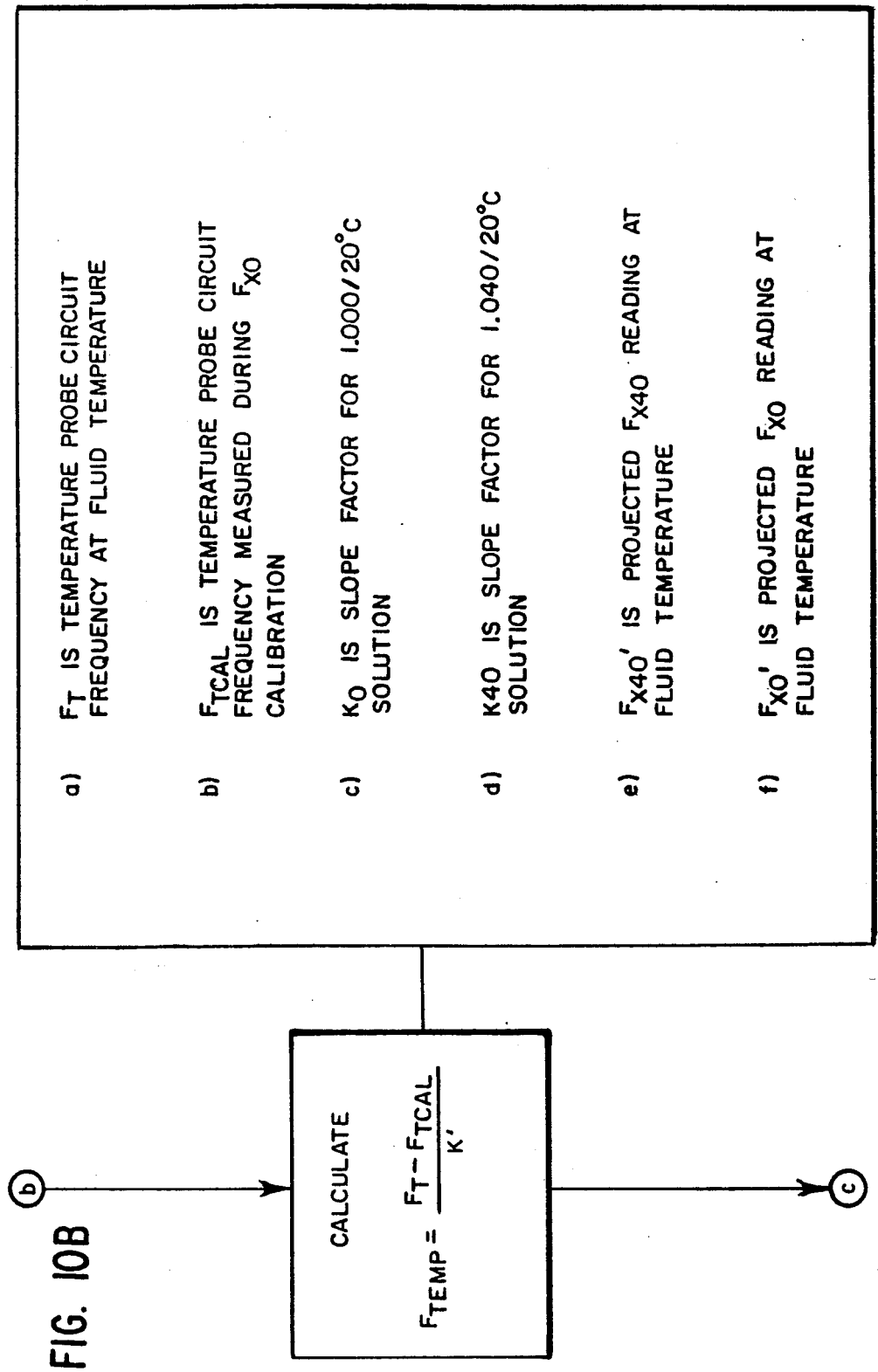

FIG. 10B a) $F_T$ IS TEMPERATURE PROBE CIRCUIT FREQUENCY AT FLUID TEMPERATURE b) $F_{TCAL}$ IS TEMPERATURE PROBE CIRCUIT FREQUENCY MEASURED DURING $F_{XO}$ CALIBRATION c) $K_O$ IS SLOPE FACTOR FOR 1.000/20°C SOLUTION d) $K40$ IS SLOPE FACTOR FOR 1.040/20°C SOLUTION e) $F_{X40}'$ IS PROJECTED $F_{X40}$ READING AT FLUID TEMPERATURE f) $F_{XO}'$ IS PROJECTED $F_{XO}$ READING AT FLUID TEMPERATURE

CALCULATE $F_{TEMP} = \dfrac{F_T - F_{TCAL}}{K'}$

BIOLOGICAL FLUID SPECIFIC GRAVITY MONITOR WITH ULTRASONIC SENSOR CIRCUIT

BACKGROUND OF THE INVENTION

This invention relates to apparatus and methods for noninvasively determining the specific gravity of a fluid, such as urine, through ultrasonic sensing techniques.

It is known to noninvasively sense the characteristics of a biological fluid in a closed collection system through the use of ultrasonic transducers. For instance, in U.S. Pat. No. 4,418,565 of St. John entitled "Ultrasonic Bubble Detector", a pair of ultrasonic transducers are located on opposite sides of a length of flexible tubing to detect air bubbles passing therethrough. Likewise, an automated urinary output monitor is shown in U.S. Pat. No. 4,448,207 of Parrish in which an ultrasonic transducer is used determine fluid level through ultrasonic echo elapsed time measurements.

However, a particular need exists to noninvasively measure the specific gravity of a fluid sample in a fluid collection system which is not achieved by the known ultrasonic sensors since they are not designed to preform this function.

SUMMRY OF THE INVENTION

Accordingly, it is a principal object of the present invention to provide an apparatus for noninvasively determining the specific gravity of urine in a urine collection system which employs ultrasonic sensors.

In a preferred embodiment, this principal objective is achieved by providing such an apparatus with means defining a chamber for holding a sample of urine, a pair of ultrasonic transducers at opposite sides of the chamber for respectively transmitting through the urine sample and receiving ultrasonic pulses and means including an oscillator with a feedback loop including the ultrasonic transducers for producing an output signal with a frequency determined by the period of time it takes for a transmitted ultrasonic pulse to travel through the urine sample and to be received and means responsive to this frequency for providing an indication of specific gravity of the urine sample. The average elapsed time and thus the frequency is dependent upon the specific gravity of the urine sample.

An advantageous method of measuring the specific gravity of urine is also provided comprising the steps of obtaining a sample of urine, operating an oscillator circuit having an ultrasonic transmitter and receiver on opposite sides of the sample at a frequency dependent upon the specific gravity of the sample and providing an indication of the specific gravity of the sample based upon said frequency.

BRIEF DESCRIPTION OF THE DRAWINGS

The foregoing objects, features and advantages of the present invention will be described in greater detail and further objects and advantageous features will be made apparent in the following detailed description of the preferred embodiment which is given with reference to the several figures of the drawing, in which:

FIG. 3A is a sectional plan view of the preferred form of the sampling chamber assembly of FIG. 1A;

FIG. 3B is a sectional side view of the sampling chamber assembly of FIGS. 1A and 3A;

FIG. 4 is a sectional side view of an alternate embodiment of the sampling chamber assembly of FIGS. 3A and 3B;

FIG. 5 is a sectional side view of a sensor probe assembly of FIG. 1;

FIGS. 10 and 10A, 10B, 10C and another logic flow chart, or algorithm, illustrating the detailed operations performed by the computer during the specific gravity temperature compensation routine of FIGS. 9A and 9B.

DETAILED DESCRIPTION

Figure 1A:
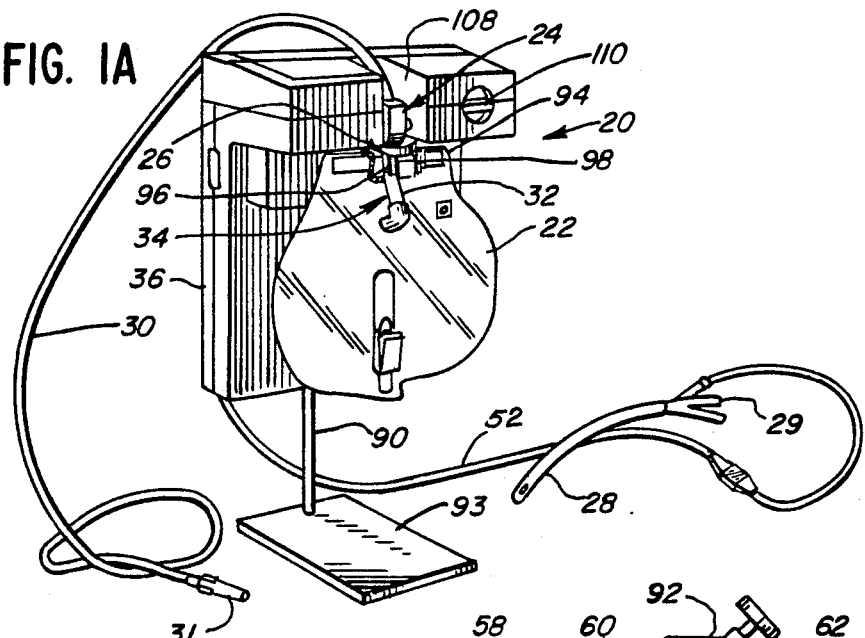
FIG. 1A is a perspective view of an automated urine output monitor, or AUOM, for weighing and making other measurements of urine collected in a flexible urinary collection bag releasibly attached thereto and with respect to which a preferred embodiment of the present invention is employed.
Figure 2:
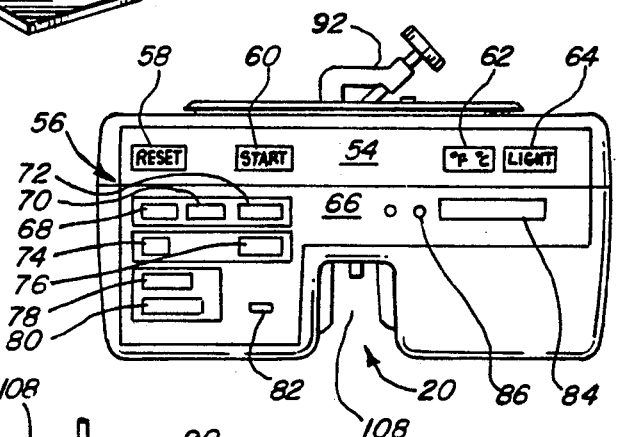
FIG. 2 is a plan view of the AUOM of FIGS. 1A and 1B showing the AUOM display and control panels.
Figure 1B:
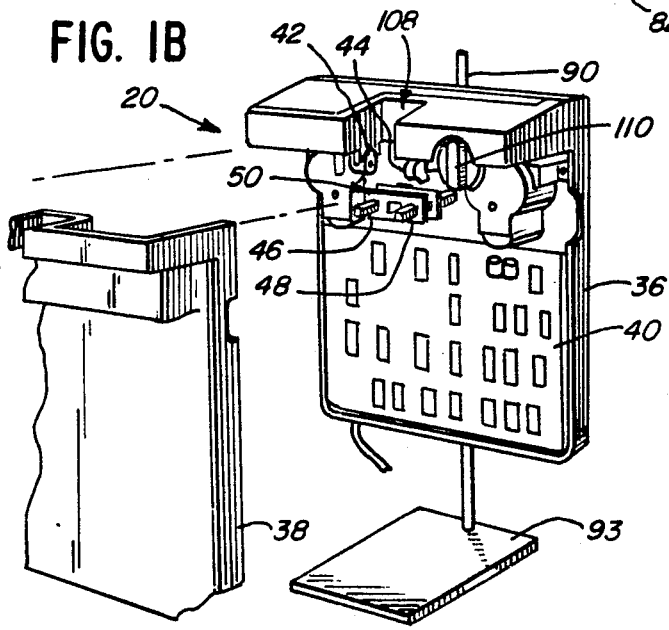
FIG. 1B is another perspective view of the AUOM of FIG. 1A but with the urinary collection bag and a front panel removed to facilitate a better view of the inner workings of the AUOM.

Referring now to the several figures of the drawing, particularly FIGS 1A, 1B and 2, an automated urine output monitor, or AUOM, 20 is seen with a flexible, plastic urinary collection bag mounted thereto by means of a sampling chamber assembly 24 and a force isolation system 26. As will be explained in greater detail, the sampling chamber assembly 24 and force isolation system 26 interconnect to form a closed fluid collection system between a patient (not shown) connected to the distal end of a Foley catheter 28 and the interior of the urinary collection bag 22. The catheter 28 is connectable by means of a catheter connector 29 and connector 31 with a flexible, plastic drainage tube 30. The other end of drainage tube 30 is in fluid communication with the sampling chamber assembly by means of a suitable tube connector located atop sampling chamber assembly 24. Fluid from sampling chamber 24 flows through a flexible conduit of the force isolation system 26 and through an angular conduit 32 of a front entry connector assembly 34.

Referring to FIG. 1B, the AUOM is seen to have a housing, comprised of a housing frame 36 with a removable front housing panel 38. This housing protectively encloses an electronic control and measurement module 40 which includes a computer and interface circuitry described below with reference to FIGS. 8, 9A and 9B. Briefly, the computer receives signals through the interface circuitry from suitable transducers associated with sensor probe assemblies 42 and 44 connectible with the sampling chamber assembly 24 for noninvasively determining both specific gravity and temperature of a urine sample contained within the chamber assembly 24. The computer is also responsive to electronic signals received through other interface circuitry from transducers associated with a pair of mounting arms 46 and 48 of a bag mounting assembly 50 to determine the weight of the urine collected within urinary collection bag 22. The computer also determines patient core temperature based on signals from a temperature transducer associated with a temperature probe within catheter 28 and connected thereto by means of an electrical cord 52. The computer also receives signals through suitable transducers indicative of the ambient temperature, the status of its D.C. portable battery supply (not shown) and signals from a control section 54 of a control and display panel 56, FIG. 2. These controls include a manually actuatable reset switch 58, a start switch 60, a temperature scale selection switch 62 and a display light actuation switch 64.

Referring to FIG. 2, the computer automatically, periodically calculates specific gravity, temperature, volume and time based upon these transducers and control input signals and causes them to be visually indicated at various electronic digital display units of a display section 66 of control and display panel 56. The volume in milliliters of the urine collected in bag 22 for the present hour, the previous hour and for all collection accumulated is indicated at display units 68, 70 and 72, respectively. Based upon appropriate signals received from either the start switch 60 or reset switch 58, and an internal clock, the computer also indicates the number of minutes elapsed since the present hour commenced and the cumulative time since the collection process started at display units 74 and 76, respectively. The specific gravity is shown on display unit 78, and core temperature, either in Fahrenheit or centigrade degrees depending upon the state of scale selection switch 62, is shown at display unit 80. A low battery condition for the portable AUOM is provided by an indicator 82, and various conditions sensed by the computer are indicated by an alphanumeric message display unit 84 and an alert indicator lamp 86.

In normal operations, the AUOM unit is releasibly attached to an upright mounting standard 90 by means of a screw clamp 92 attached to the back of housing 36. Although standard 90 may be mounted to its own floor supported base member 93, as shown, preferably standard 90 is releasably mounted to the patient's bed in a manner shown in U.S. patent application of James R. Gross, Ser. No. 684,238, filed Dec. 20, 1984, entitled "Medical Equipment Mounting Apparatus" filed contemporaneously herewith and assigned to the assignee of this application.

The catheter set, consisting of catheter 28, catheter drainage tube 30, sampling chamber assembly 24, force isolation system 26, front entry connector assembly 34 and collection bag 22 are brought to the patient and the patient is catherized. After the AUOM unit has been mounted in a correct location for the patient and after the catherization procedure, the urinary collection bag 22 is taken to the AUOM unit 20 and mounted. The force isolation system 26 includes a relatively rigid header assembly 94 having a pair of spaced female connectors 96 and 98 which are adapted for mating receipt of mounting arms 46 and 48, respectively, to suspend the collection bag 22 therefrom. As shown and described in the U.S. patent application of Robert M. Sakai and William J. Dunn, Ser. No. 730,736, filed May 6, 1985, entitled "Suspension Mounting Apparatus for Biological Fluid Collection Bag", filed contemporaneously herewith and assigned to the assignee of this application, means are provided for causing arms 46 and 48 to interlock with female connectors 96 and 98.

The arms 46 and 48, in turn, are connected to a weight measuring transducer, such as a strain gage, of a weigh scale circuit 368 described below with reference to FIG. 7. Further information concerning the force isolation system 26 can be obtained by reference to one or more of U.S. patent applications entitled "Apparatus With Force Isolation For Measuring Weight of Collected Fluid and Method" oi Brian H. Silver; Ser. No. 739,230, filed May 6, 1985, "Force Isolation Apparatus With Limit Restraint for Fluid Collection System" of Brian H. Silver and William J. Dunn Ser. No. 730,739, filed May 5, 1985; "Force Isolation Apparatus With Cuff Forming Conduit For Biological Fluid Collection System" of James R. Gross and William Dunn Ser. No. 684,237, filed Dec. 20, 1984; and "Connection Apparatus for Side Connection to Fluid Collection Bag" of Lucien M. Rath and William J. Dunn Ser. No. 583,993, filed Dec. 20, 1984.

After a pair of protective sensor caps 102, only one of which is shown in FIG. 3A, are from a pair of relatively rigid probe guide connectors 229 and 228, the probe guide connectors 229 and 228 are enabled for mating receipt of sensor probe assemblies 42 and 44, respectively. Also, once caps 102 are removed, the sampling chamber assembly 24 is enabled for receipt within a sensing location 108 with sensor probe guide connectors 104 and 106 located respectively opposite sensor probes 42 and 44. The collection bag 22 is locked onto arms 46 and 48, as explained more fully in U.S. patent application of Robert M. Sakai and William J. Dunn entitled "Suspension Mounting Apparatus For Biological Fluid Collection Bag" Ser. No. 730,736, filed May 6, 1985.

The two sensor probe assemblies 42 and 44 are then caused to move together through manual actuation of a probe actuator 110. When the actuator 110 is moved from its position as shown in Fig. 1B to the operative position shown in FIG. 1A, the two sensor probes move together and respectively matingly engage the sensor probe guide connectors 104 and 106. Since the drainage tube 30 is mounted to sampling chamber assembly 24, both the chamber and the downstream end of the drainage tube 30 are held against movement relative to the housing frame 36. After this is done, the start switch 60 is actuated and the AUOM unit 20 begins operations to provide the monitor information described above.

Referring still to FIGS. 3A and 3B, the sampling chamber assembly 24 has a sampling chamber 170 attached to and contained within a sampling chamber housing 172 intermediate a housing inlet 174 and an outlet 176. The inlet 174 is connected in fluid communication with the open end 177 of drainage tube 30 by means of an annular inlet connector 178. After the flexible drainage tube 30 is inserted into mating relationship with connector 178, the connection is rendered permanent by means of applying adhesive, causing preapplied adhesive to set, solvent bonding or the like. The housing outlet 176 is connected to an inlet end of the elongate conduit 148. The outlet 142 of conduit 148 is coupled through means of the connector 140 with the flexible diaphragm connector of the force isolation system 26, as disclosed above and in the above referenced patent applications, to form a closed fluid collection system between the housing inlet 174 and the interior of the urinary collection bag 22.

As best seen in FIG. 3B, the sampling chamber 170 is a trough-shaped member having an open top 171 defined in part by edges 180 and 182 of a pair of opposite walls of chamber 170. This open top is situated at a position beneath the housing inlet 174, so that fluid from the open end 177 of drainage tube 30 falls into the open top 171 and the open top thus comprises an inlet for sampling chamber 170. New fluid entering this inlet replenishes and mixes with any fluid previously stored in the chamber. Once the fluid has filled sampling chamber 170, the addition of more fluid will cause some of the previously received fluid to overflow one or both of edges 180 and 182. Thus, the open top 171 also functions as an outlet for sampling chamber 170.

The opposite walls of the sampling chamber 170 are preferably integrally formed of plastic together with the sampling chamber housing 172, the annular inlet connector 178 and the elongate conduit 148. Preferably, the plastic is transparent, so the fluid in the chamber housing 172 and sampling chamber 170 is accessible to visual monitoring.

As noted above, the fluid sampling chamber has a pair of opposed, sensor walls 186 and 188. These walls also comprise exterior walls of the housing 172, so that they are accessible to sensors, such as an ultrasonic emitter of sensor probe assembly 42, located outside of the housing for making non-invasive measurements of characteristics of the fluid within the sampling chamber 170. Preferably, the distance between sensor walls 186 and 188 is selected for optimum sensing of the fluid being sensed. For sensing the specific gravity of human urine, a distance on the order of 1.0 inch has been found suitable for sensing with the ultrasonic "sing-around" circuit of FIG. 6.

Since the fluid is continuously being replenished with fresh fluid during the collection process, continuous in-line measurements are made on fresh samples. Preferably, erroneous readings due to the accumulation of particulate matter settling out of suspension from the fluid are avoided by providing the sampling chamber with a sediment trap 190 located beneath the sensing level of the sensor walls 186 and 188.

The sensor walls 186 and 188 preferably comprise relatively thin, flexible, resilient membranes which are mounted to the relatively rigid bosses 192 and 194, respectively, to close circular sensor wall openings at the opposite sides of sampling chamber housing 172 and sampling chamber 170. These membranes are made from flexible plastic, rubber or other suitable material which has an ultrasonic transmission characteristic comparable to that of the fluid being sensed. For sensing human urine, urethane plastic has been found to be suitable.

When the sampling chamber 170 is employed with a sensor probe, such as that shown in FIG. 5, which has a temperature sensor, described below, the flexible sensor walls 186 and 188 are selected to have a relatively high heat conduction characteristic which is not substantially less than that of the remainder of the walls of chamber 170 and chamber housing 172. Sensor walls made of the plastic noted above have been found suitable for this purpose.

Referring still to FIGS. 3A and 3B, an acoustic coupling agent assembly is provided to enhance good airless coupling between the sensor probe assemblies 42 and 44 and the sensor walls 186 and 188. This assembly comprises an acoustic coupling agent 196 on the outside surface of the sensor walls 186 and 188 and a relatively thin coupling agent distribution member 198 overlying the sensor wall 186 or 188. The thin distribution member 198 is preferably made of coupling agent-absorbent, flexible, paper-like, material. If so, some of the fluid coupling agent 196 is absorbed within the distribution member. Preferably, the coupling agent 196 is a fluid such as an oil-like substance, or silicone fluid. For acoustic coupling with sensor wall 186 and 188 made of material having acoustic transmission characteristics matched to human urine, the use of paper, such as used for tea bags, for the distribution member with DOW 710 Silicon fluid from Dow Chemical Co. as a coupling agent has been found to be satisfactory.

With respect to the configuration of the thin distribution member 198, it is a disc with a generally circular shape which matches that of the sensor probes 42 and 44 and the sensor walls 186 and 188. Preferably, the thin member 198 has cuts which form pie-shaped notches or which simply form radial slits to facilitate the flexible movement of the thin member 198 with that of the sensor wall 186 or 188 to avoid wrinkling and possible resultant air gaps. Reference to U.S. patent application of Brian H. Silver and Fred M. Rasmussen, Ser. No. 733,083, filed May 6, 1985, entitled "Acoustic Coupler With Assembly Coupling Agent for Noninvasive Sensing of Sampling Chamber Fluid" and of William J. Dunn and Brian H. Silver, Ser. No. 731,094, filed May 6, 1985, entitled "Acoustic Coupling Assembly With Retaining Connector for Noninvasive Sensing of Sampling Chamber Fluid", filed contemporaneously herewith and assigned to the assignee of this application, should be made for further information concerning the acoustic coupling assembly.

Referring again to FIGS. 3A and 3B, relatively rigid connector member 228 and 229 is mounted to the chamber assembly 24 around each of the sensor walls 186 and 188. These connectors 228 have an access opening 230 for coupling engagement therethrough of a transducer, or probe, tip 232, shown in FIG. 5, of sensor probe assembly 44. In addition, connector 228 includes an annular shoulder portion 234 in retentive overlying relationship with the acoustic coupling agent assembly including the coupling agent 196 and the relatively thin coupling agent distribution member 198. This shoulder portion 234 simply blocks the distribution disc 198 from passage through the access opening 230 or the fluid coupling agent 196 from flowing out of the access opening 230 and away from adjacency to the sensor wall 186 or 188. The diameter of the distribution disc 198 is greater than that of the access opening 230.

The connector member also has a conical or partially spherical guiding surface 238 for guiding and then snugly seating the forward part of a partially spherical probe housing, or guide, 240 of sensor probe assembly 42 or 44 to a position in which the probe tip 232 is directly opposite and insertable through the associated access opening 230, as seen in FIG. 3A.

As the sensor probe assemblies 42 and 44 are moved together to their operative position, the guide surfaces 238 being engaged by the spherical probe housing 240 causes the access opening 230 to become aligned with the probe tips 232. The connector also has an exterior cylindrical connector surface 241 for releasable mating connection with protective sensor cap 102. Further information concerning these features is obtainable by reference to U.S. patent application of Terry D. Lewis Ser. No. 683,989, filed Dec. 20, 1984, entitled "Mechanism for Proper Alignment of Sensor Probes With Fluid Sample Chamber" filed contemporaneously herewith and assigned to the assignee of the present invention.

The chamber assembly 24' of FIG. 4 is different from the chamber assembly 24, in that it includes an inverted U-shaped siphon tube 220. Unlike the chamber assembly 24, this siphon tube 220 causes the entire fluid contents of sampling chamber 222 to be flushed out of the chamber and through the tube 220 and an outlet 224 when the fluid level reaches the level 226 of the inverted U-portion of the siphone tube 220. As in sampling chamber assembly 24, all fluid passes through the sampling chamber 222, since there is no alternative communication between the inlet 226 and the outlet 224.

Referring now to FIG. 5, each of the sensor probe assemblies 42 and 44 includes a transducer 284. It has a transducer housing 286 which is slideably received within an axial bore 288 of the probe housing 240 at one end and is connected to and carried by the appropriate one of a pair of arms such as described in U.S. patent application of Terry D. Lewis entitled "Mechanism For Proper Alignment of Sensor Probes with Fluid Sample Chamber" Ser. No. 683,989, filed Dec. 20, 1984, assigned to the assignee of this application. As above, the sensor probe housing 240 and guide surface mate with one another to cause the symmetrical engagement of pair of female guide surfaces 238 of connector member 228 by probe housing to correctly align the chamber assembly 24 to the probes for proper sensing. While spherical surf for the probe housing 240 and guide surface 238 work fine, conical surfaces will work as well to achieve the desired automatic alignment through engagement.

After the mating engagement of the probe housing 240 with the guide surfaces 238 stops further relative movement therebetween, the sensor probe housings continues to move toward one another until otherwise blocked against further movement when a preselected distance is reached, as described in the aforementioned patent application of Terry D. Lewis. As they continue to move, each of the probes slideably move within its associated bore 288 from an inoperative position in which the probe tip 232 is protectively recessed within the bore 288, as shown in FIG. 5 in solid line, to an operative position 290, shown in broken line, in which the probe tip 232 protrudes from the end of the probe guide housing 240. A coil spring 292 bears against a shoulder 293 of axial bore 288 and one of the aforementioned pair of arms 295 to which transducer housing 286 is attached to resiliently bias the probe toward its protected inoperative position. Accordingly, when the probe guide 240 is disengaged from guide surface 238, it automatically recedes within the bore 288.

The bore 288 has an annular shoulder 294 adjacent its forward end against which an annular collar 296 of transducer housing 286 resiliently seats when the is in its inoperative position.

The sensor walls 186 and 188, when in an unflexed state, are spaced from one another by a preselected distance which is slightly greater than the distance between the probe tips when they have been moved to the preselected distance noted above. Accordingly, the probe tips 232 resiliently press thereagainst to assist in the removal of any gaps therebetween. Since the sensor walls 186 and 188 are flexible, the sampling chamber assembly dimensions do not establish the preselected distance between the probe tips. This critical distance can therefore be maintained constant for different measurements with different sampling chambers despite minor variations in the distances between the sensor walls.

The transducer, when an ultrasonic transducer is used, comprises an ultrasonic crystal disc 298 mounted at the end of probe tip 232 to close the opening at the end of housing 286. If it is the emitter, electrical signals are applied to the crystal disc 298 via a pair of leads 297 to cause ultrasonic vibrations of the disc 298. If it is the receiver, vibrations of the disc 298 are converted thereby to electrical signals which are connected to the amplifier 306 of FIG. 6.

In addition to the acoustic transducer, a temperature sensing transducer 299, such as a thermistor, is mounted within probe housing 286. As seen, the end of the probe is in physical contact with the interior side of disc 298 and thus senses the temperature of the sensor walls and fluid through the disc 298. This decreases response time but does not significantly interfere with the ultrasonic transducing characteristic of the disc 298. Preferably, the temperature transducer 299 is contained within the receiving transducer housing 286, and the disc and sensor walls are selected to have good heat conduction characteristics.

Figure 6:
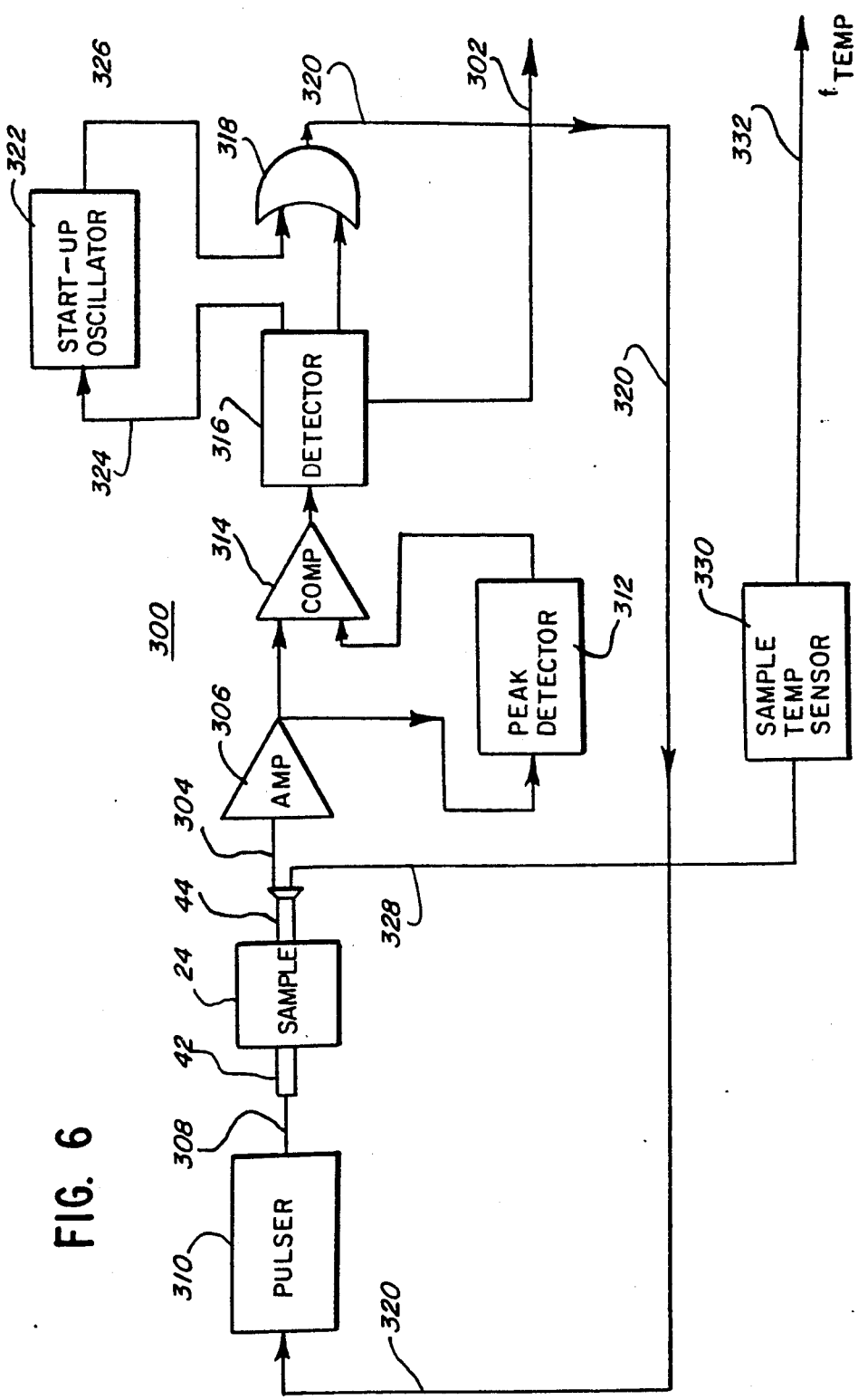
FIG. 6 is a schematic block diagram of a preferred embodiment of an ultrasonic sensing circuit with a temperature sensor circuit useable in conjuction with the sensor probe assembly of FIG. 5.

Referring to FIG. 6, the sensor probe assemblies form part of a "sing around" ultrasonic oscillator, or sensor circuit, 300. Sensor circuit 300 produces an output signal on its output lead 302 which has a frequency that varies in a known relationship with variations of the specific gravity of the sample within sampling chamber assembly 24. More specifically, it varies in accordance with the elapsed time for an ultrasonic pulse generated by the emitting sensor probe assembly 42 to pass through the fluid sample within sampling chamber assembly 24 and be received by the receiving sensor probe assembly 44. This ultrasonic conduction characteristic is a function of the specific gravity, or relative density, of the sample within sampling chamber assembly 24. These ultrasonic pulses received by sensor probe 44 are converted into electrical signals on lead 304 applied to an amplifier 306 of circuit 300. The remainder of circuit 300 responds to these signals to cause production of pulser signals on output lead 308 from a pulser circuit 310. These pulser signals are converted into ultrasonic vibrations by sensor probe assembly 42 that are transmitted through the sample of chamber assembly 24 to form a closed loop.

The feedback path between amplifer circuit 306 and pulser circuit 310 includes a peak detector circuit 312, a comparator circuit 314, a detector circuit 316, an OR-gate 318, and a feedback lead 320 interconnecting the output of the OR-gate 318 with the pulser circuit 310.

Initially, prior to start-up of circuit 300, no pulses are received from comparator circuit 314, and thus no pulses are produced by OR-gate 318 in response to detector circuit 316. However, detector circuit 316 detects the absence of pulses from comparator circuit 314 to actuate a start-up oscillator circuit 322 through application of an input signal thereto through input lead 324. Once the start-up oscillator begins operating, it produces start-up pulses on its output lead 326. These start-up pulses are passed by the OR-gate 318 to actuate pulser circuit 310.

If there is no fluid in the sampling chamber assembly 24, or another problem exists which prevents proper pulses from being received by sensor probe assembly 44, this condition will be sensed by the detector circuit 316, and the start-up oscillator circuit 322 will continue to operate.

However, if conditions are correct for sensing, the first pulse generated by the pulser 310 will result in production of an amplified pulse at the input of peak detector 312. This first pulse will partially charge a capacitor (not shown) of the peak detector circuit 312. After several such start-up pulses, the peak detector circuit 312 will have accumulated a charge equal to its average DC value. The comparator circuit 314 then responds to the output pulses from amplifier 306 by producing very narrow output pulses on its output which are applied to detector 316.

The detector circuit 316 then determines if the pulse repetition rate of the signals from comparator 314 are within the "sing around" frequency range for the fluid being sensed. If so, it applies a signal to the input lead 324 which disables, or turns off, start-up oscillator. The output 326 of start-up pass pulses from detector 316 to the feedback lead 320 and pulser 310.

Once this occurs, the sensor circuit 300 inherently oscillates, or generates its feedback signal, at a rate determined by the elapsed time for the transmitted pulse to travel through the fluid and be received. The electronic circuit delay is preferably less than 0.3% of the elapsed time of pulses through the chamber assembly 24 and thus has little effect on the frequency of oscillation Variations in amplitude of received ultrasonic signals caused by variations in the acoustic coupling with disposable sampling chamber assemblies and variation in temperature are accommodated by the peak detector 312. For this purpose, peak detector 312 is a high speed detector with means for automatically maintaining the same receive burst threshold point for wide variations in amplitude. This enables accurate readings even under poor ultrasonic and coupling conditions. A two point calibration system is provided with specific generation of calibration points at approximately 1.000 and 1.040 to calibrate each instrument. The circuit is also preferably designed to have a high rejection of power supply variation effects. A power supply rejection ratio of approximately 58 db has been found suitable.

Sensor probe assembly 44 also includes a temperature transducer which produces a signal on sensor leads 328 representative of the temperature of the sample in sampling chamber assembly 24. Like output 320, the temperature sensor circuit 330 converts the analog signal applied to its input lead into an oscillating signal on its output 332. This oscillating signal has a frequency which is representative of the temperature of the sample. As will be explained, this temperature compensation signal is provided to the AUOM computer which is responsive to both the oscillator output signal on output lead 302 and the temperature connection signal on output lead 332 to provide an indication of the specific gravity of the urine sample or other fluid which is compensated for variations from a standard temperature. The frequency of the temperature compensation signal has a frequency which has a known relationship to the amount of compensation required for a given temperature.

Figure 7:
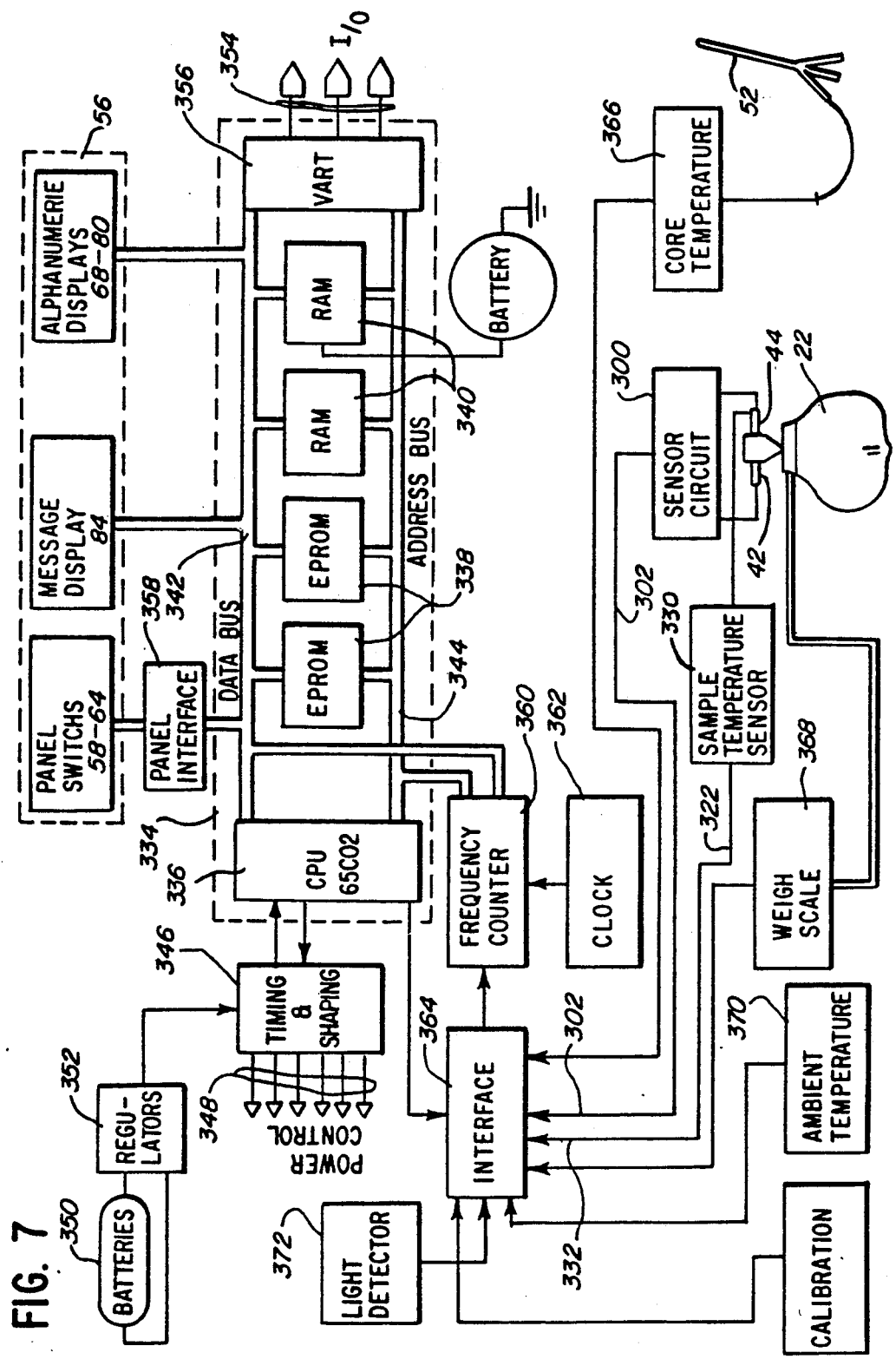
FIG. 7 is a functional block diagram of the AUOM of FIGS. 1A, 1B, and 2 including the computer of FIG. 1B.

Referring now to FIG. 7, the AUOM circuitry is seen to include a microcomputer 334 comprising a central processing unit, or CPU, 336 interconnected with a pair of erasable programmable read only memories or EPROMs 338 and a pair of random access memories or RAMs 340 interconnected with the central processing unit 336 through a data bus 342 and an address bus 344. Suitable timing and shaping circuits 346 provide appropriate timing signals to the central processing unit 336 and provide appropriately shaped power control output signals on a plurality of power control outputs 348. DC power is provided to the timing and shaping circuits 346 by batteries 350 or the like through suitable regulator circuits, or regulators 352. Input/output ports 354 are provided by means of a UART circuit 356 connected with data bus 342 and address bus 344. Various elements of the control and display panel 56, such as panel switches 58, 60, 62 and 64, the message display unit 84 and the other display units 68, 70, 72, 74, 76, 78 and 80 also interconnect with the computer 334. The message display unit and the other display units interconnect directly with the data bus 342 to receive serial data therefrom, while signals between the panel switches 58-64 and the data bus 342 first pass through a panel interface circuit 358.

All the remaining inputs to the microcomputer 334 from the various sensors are obtained through a frequency counter circuit 360 which is interconnected with both the data bus 342 and the address bus 344. The frequency counter 360 receives a clock signal from a clock circuit 362 and receives all of the sensor information through an interface circuit 364 including the specific gravity output signal from sensor circuit 300 and the sample temperature signal output of the sample temperature sensor 330 of FIG. 6.

Sensor signals are applied to the interface circuit 364 by a patient core temperature sensor circuit 366, a weigh scale circuit 368, an ambient temperature sensor circuit 370 and a light detector circuit 372. Calibration is provided by means of inputs from a calibration circuit 374. The frequency of the output signals of each of these circuits is converted by the interface circuit 364 and frequency counter 360 to appropriate digital signals suitable for processing and storage by the microcomputer 334. This is done in a manner shown in the algorithms of FIGS. 8, 9A and 9B and 10.

Figure 8:
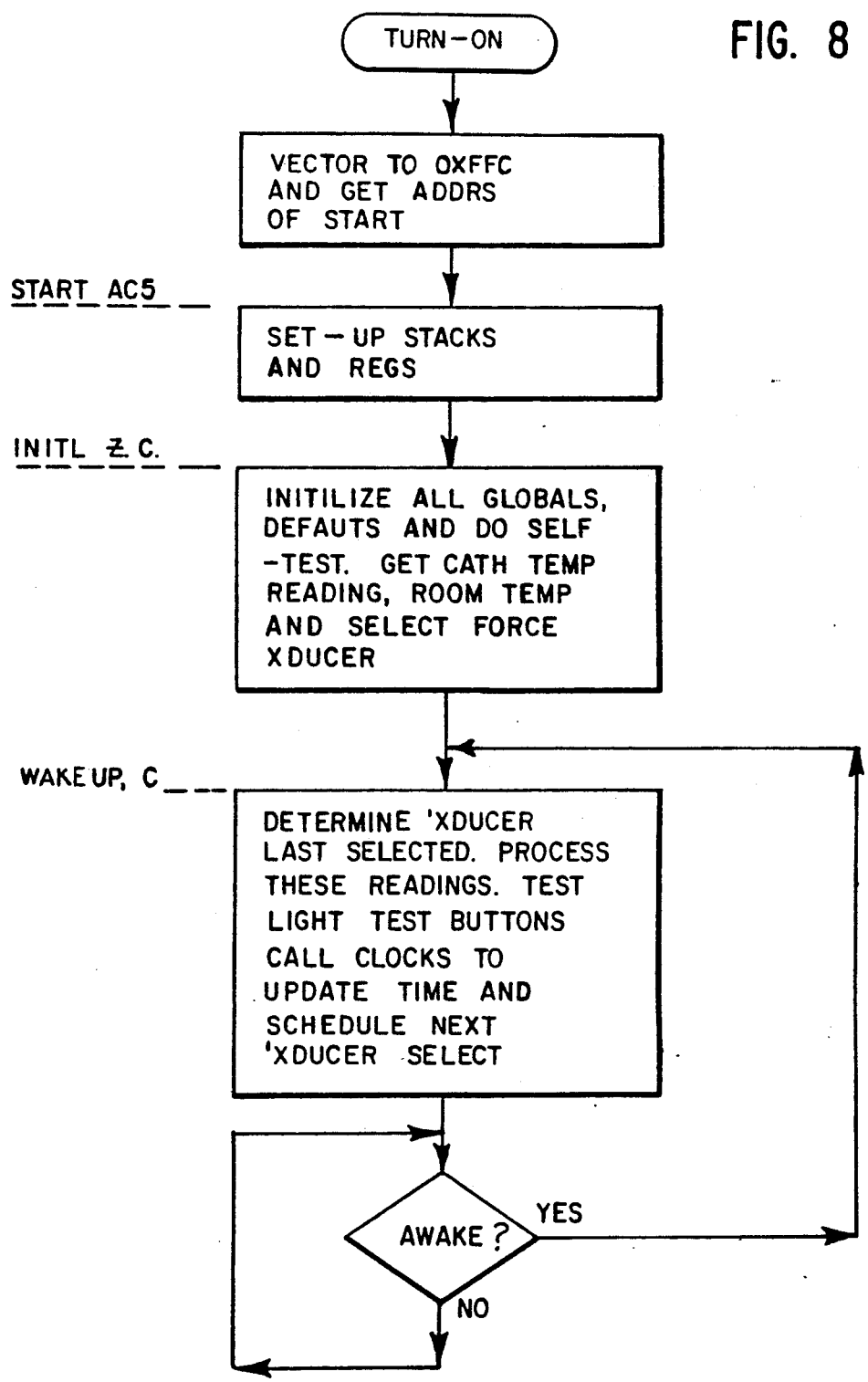
FIG. 8 is a logic flow chart, or algorithm, for start up initialization and wake-up operations of the computer of FIG. 7.
Figure 9A:
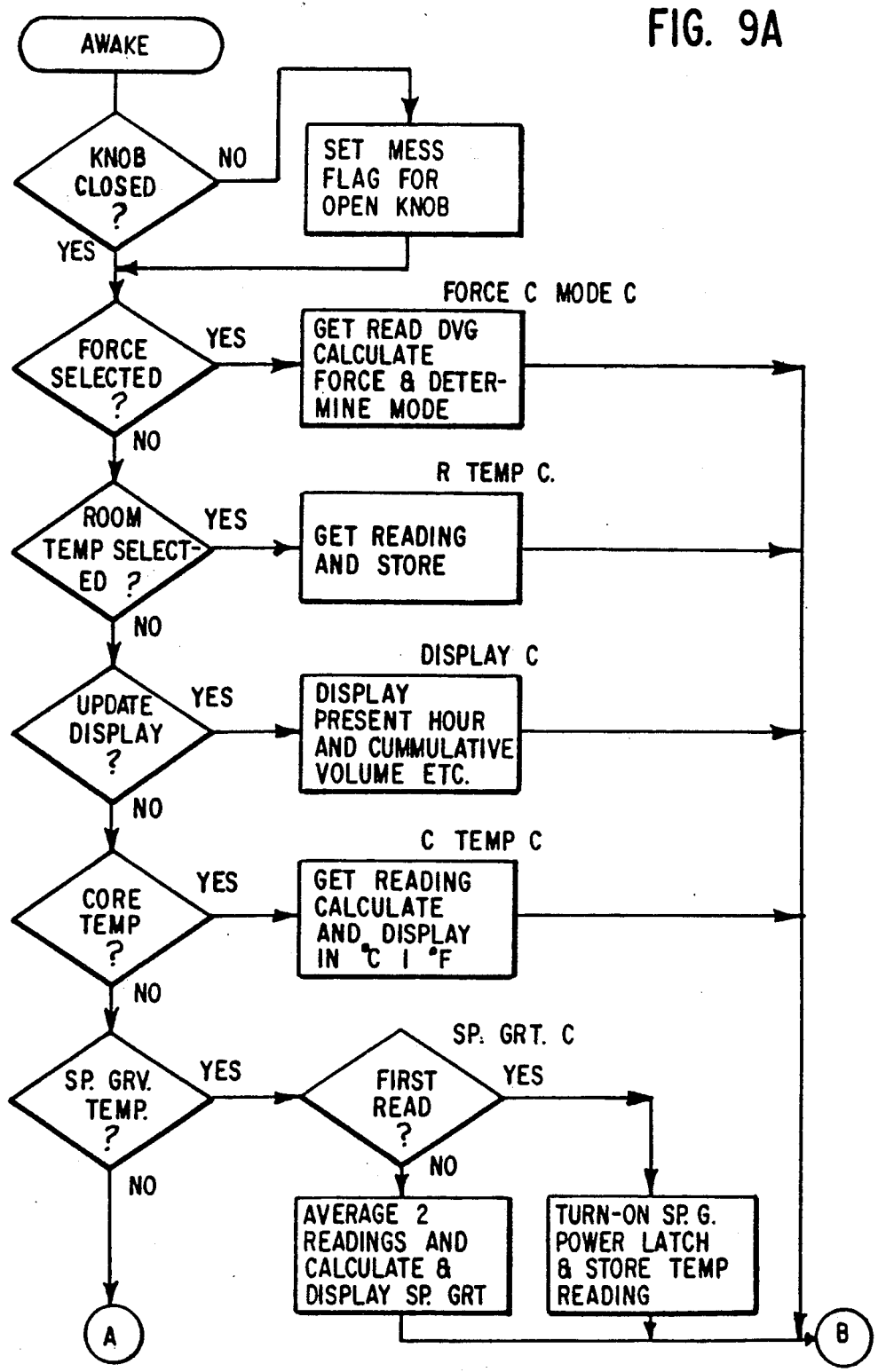
FIGS. 9A and 9B together constitute another logic flow chart, or algorithm, illustrating the detailed operations performed by the computer during the wake-up routine of FIG. 8.
Figure 9B:
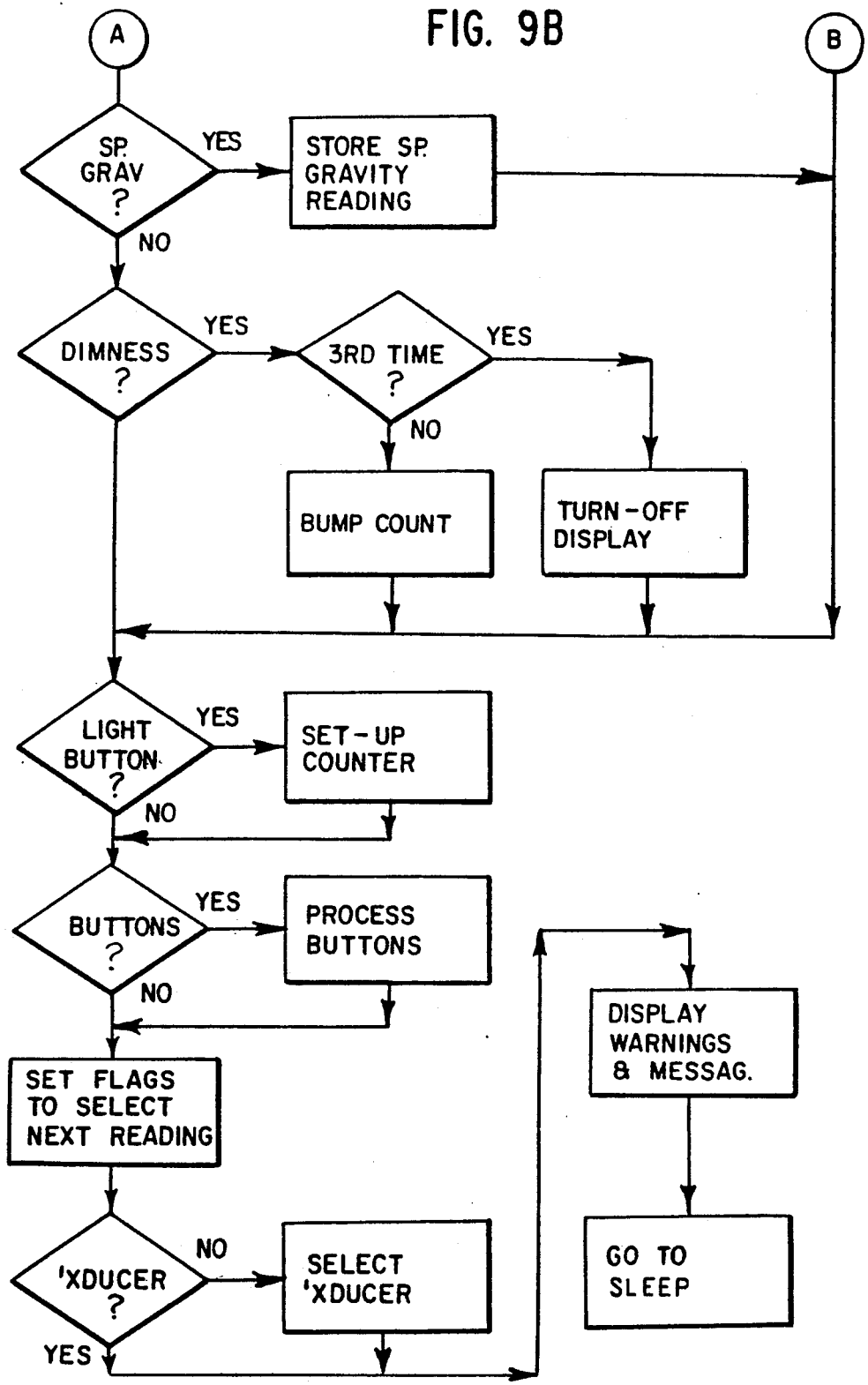
Figure 10:
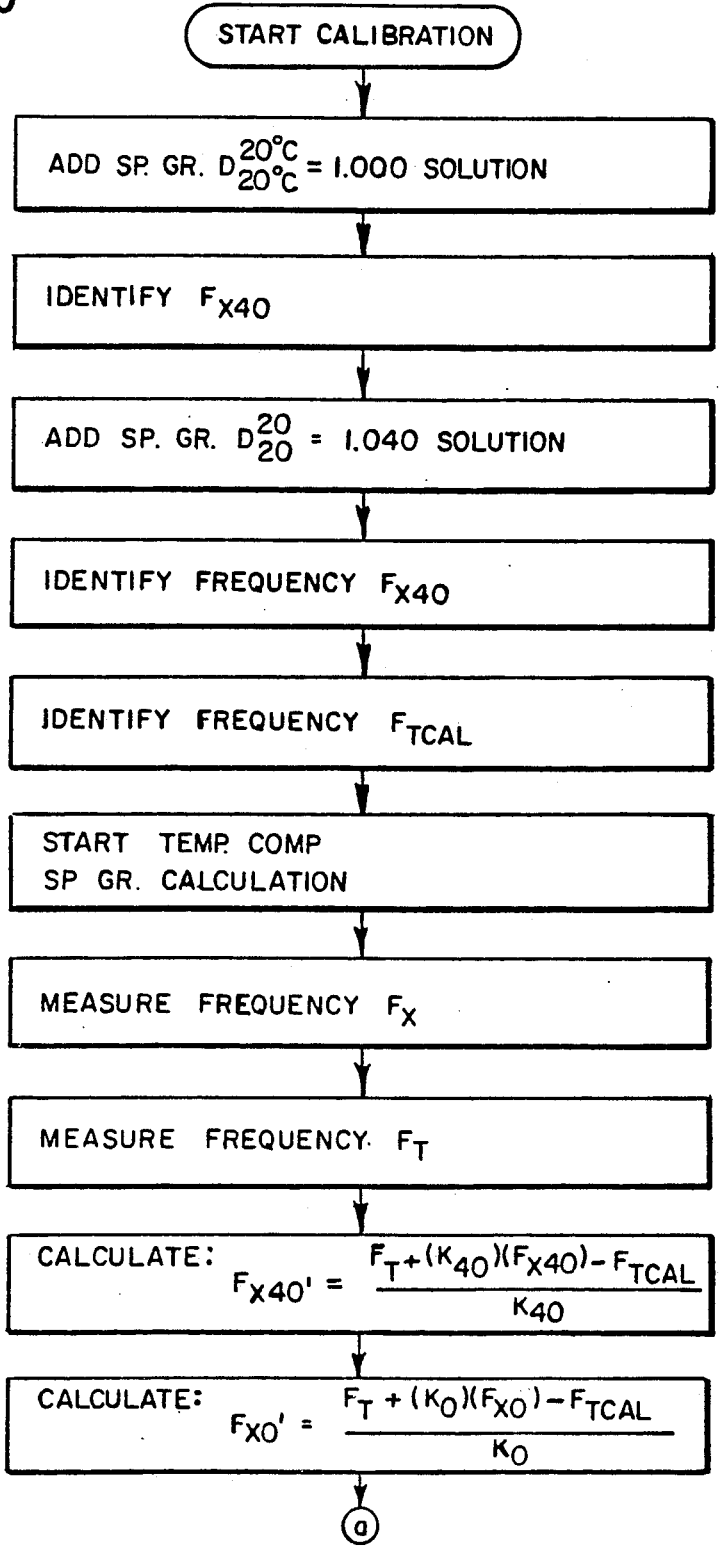
Figure 10C:
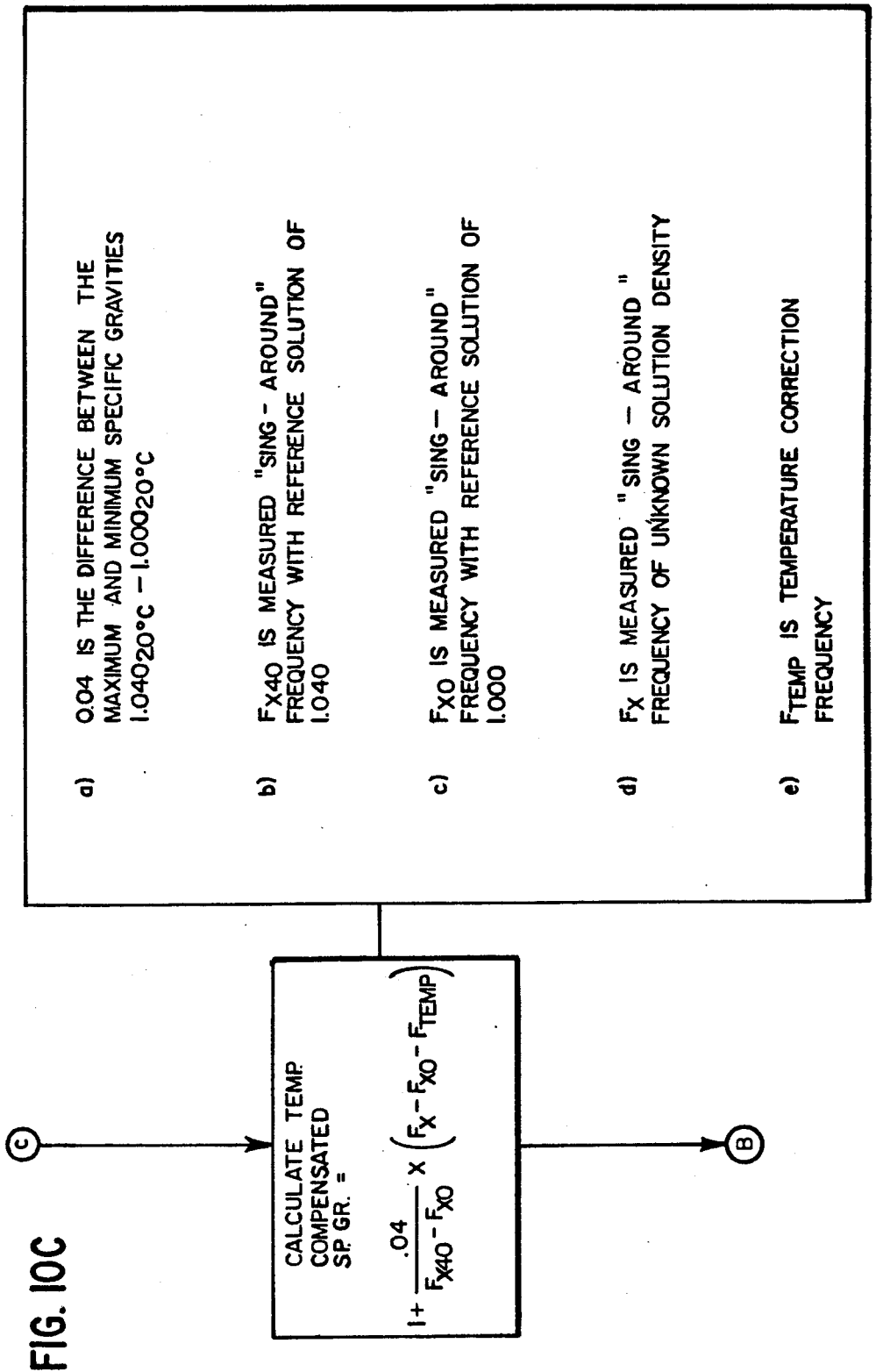

During operation of the AUOM in accordance with the algorithm of FIGS. 8, 9A and 9B, the information from a specific gravity temperature chart is stored in one of the EPROM's 338. After two temperature readings are taken, the readings are averaged and used to look up a specific gravity compensation figure on the chart which is then used to calculate or otherwise determine a temperature compensated specific gravity based on this information and the sensed or measured specific gravity. Alternatively, an empirically determined formula is stored and the temperature compensated specific gravity is calculated in accordance with the stored formula and the measured specific gravity.

The computer also responds to the patient core temperature signals obtained from patient core temperature circuit 366 and provided to it through interface circuit 364 to determine the patient core temperature and display the temperature in centigrade or Fahrenheit degrees.

The frequency of the output signal on lead 302 used to determine the specific gravity measurement is determined during a preselected time period on the order of one second to minimize the error due to transients or artifacts. The sensor circuit 300 is turned off except during periodic updating. The display of the average measurement of specific gravity is also automatically, periodically updated with new data on the order of once every half hour.

While a particular embodiment has been disclosed, this disclosure is merely for purposes of illustration of the invention as used in its present best mode, and the invention is therefore not limited thereto but is defined by the following claims.

We claim:

1. An apparatus for noninvasively determining the specific gravity of urine in a urine collection system, comprising;
   means for collecting urine samples in a closed collection system including a chamber for holding a sample of urine;
   means for noninvasively determining the specific gravity of urine collected in said chamber including an oscillator having a feedback loop with an ultrasonic transducer for producing a specific gravity signal with an average frequency determined by the average period of the time it takes for a transmitted ultrasonic pulse to travel through the urine sample and be received;
   means for generating a weight signal with a frequency representative of the cumulative weight of a plurality of collected urine samples; and
   means including a microprocessor for receiving both the specific gravity signal and the weight signal, which is responsive to the frequency of the specific gravity signal for determining the specific gravity of the urine samples and responsive to the frequencies of both the specific gravity signal and the weight signal to determine the cumulative volume of the plurality of collected samples.

2. The apparatus of claim 1 in which the frequency of said specific gravity signal received at said microprocessor is intermittently determined during Preselected time periods on the order of one second to reduce error due to transients or artifacts.

3. The apparatus of claim 1 in which said microprocessor includes
   means for periddically updating the determination of specific gravity in accordance with measurements of fresh samples;
   means for storing the specific gravity determined prior to update; and
   means for employing the same stored specific gravity with successive cumulative weight signals to determine cumulative volume.

4. The apparatus of claim 1 in which said urine collection system includes a flexible collection bag in which the successive samples are stored after specific gravity measurements thereof are made and said weight signal generating means generates a signal with a frequency representative of the weight of all the samples contained in said flexible storage bag.

5. The apparatus of claim 4 in which said flexible collection bag is suspended from a support means associated with said weight signal generating means.

6. A method of measuring the specific gravity of urine, comprising the steps of:
   (1) successively obtaining samples of urine;
   (2) operating an oscillator circuit with an ultrasonic transducer at a frequency dependent upon the specific gravity of at least some of the samples;
   (3) generating in said circuit a cumulative weight signal with a frequency representative of the weight of a plurality of said samples;
   (4) determining, by a microprocessor in the circuit, the specific gravity of the sample based upon said frequency; and
   (5) determining, by the microprocessor in the circuit, the volume of said plurality of samples based on the frequencies of both the oscillator and the cumulative weight signal.

* * * * *